US008961520B2

(12) United States Patent
Sidebotham et al.

(10) Patent No.: US 8,961,520 B2
(45) Date of Patent: Feb. 24, 2015

(54) MEDICAL CUTTING TOOL QUALITY CONTROL SYSTEMS AND METHODS

(71) Applicants: Christopher G. Sidebotham, Boonton, NJ (US); Leon Roitburg, East Hanover, NJ (US); Randall J. Lewis, Bethesda, MD (US)

(72) Inventors: Christopher G. Sidebotham, Boonton, NJ (US); Leon Roitburg, East Hanover, NJ (US); Randall J. Lewis, Bethesda, MD (US)

( * ) Notice: Subject to any disclaimer, the term of this patent is extended or adjusted under 35 U.S.C. 154(b) by 261 days.

(21) Appl. No.: 13/688,004

(22) Filed: Nov. 28, 2012

(65) Prior Publication Data
US 2013/0150860 A1    Jun. 13, 2013

Related U.S. Application Data

(60) Provisional application No. 61/564,263, filed on Nov. 28, 2011.

(51) Int. Cl.
*A61B 17/00*  (2006.01)
*A61B 17/16*  (2006.01)
*A61B 19/00*  (2006.01)

(52) U.S. Cl.
CPC ......... *A61B 17/1666* (2013.01); *A61B 17/1659* (2013.01); *A61B 17/1617* (2013.01); *A61B 2019/4815* (2013.01); *A61B 2019/4873* (2013.01)
USPC .............................................. 606/81; 606/80

(58) Field of Classification Search
USPC ....................................................... 606/80, 81
See application file for complete search history.

(56) References Cited

U.S. PATENT DOCUMENTS

| 5,313,935 | A | 5/1994 | Kortenbach et al. |
|---|---|---|---|
| 5,359,993 | A | 11/1994 | Slater et al. |
| 5,448,042 | A | 9/1995 | Robinson et al. |
| 5,519,197 | A | 5/1996 | Robinson et al. |
| 5,991,355 | A | 11/1999 | Dahlke |
| 6,113,392 | A | 9/2000 | Braun |
| 7,048,687 | B1 | 5/2006 | Reuss et al. |
| 7,186,966 | B2 | 3/2007 | Al-Ali |
| 2005/0121350 | A1 | 6/2005 | Bogren et al. |
| 2005/0178460 | A1 | 8/2005 | Magno, Jr. |
| 2006/0286506 | A1 | 12/2006 | Birnholtz |
| 2008/0244909 | A1 | 10/2008 | Golan et al. |

*Primary Examiner* — Andrew Yang
(74) *Attorney, Agent, or Firm* — Klarquist Sparkman, LLP

(57) ABSTRACT

A cutting tool includes a cutting surface on a first side and an attachment member on a second side. The attachment member is configured to be coupled to a powered driving member. The cutting tool includes a limiting device configured to restrict the use of the cutting tool to a predetermined number of uses. The limiting device can be configured to restrict the number of uses of the cutting tool by restricting the number of times that the attachment member can be coupled to the powered driving member.

29 Claims, 9 Drawing Sheets

FIG. 4C  FIG. 4B

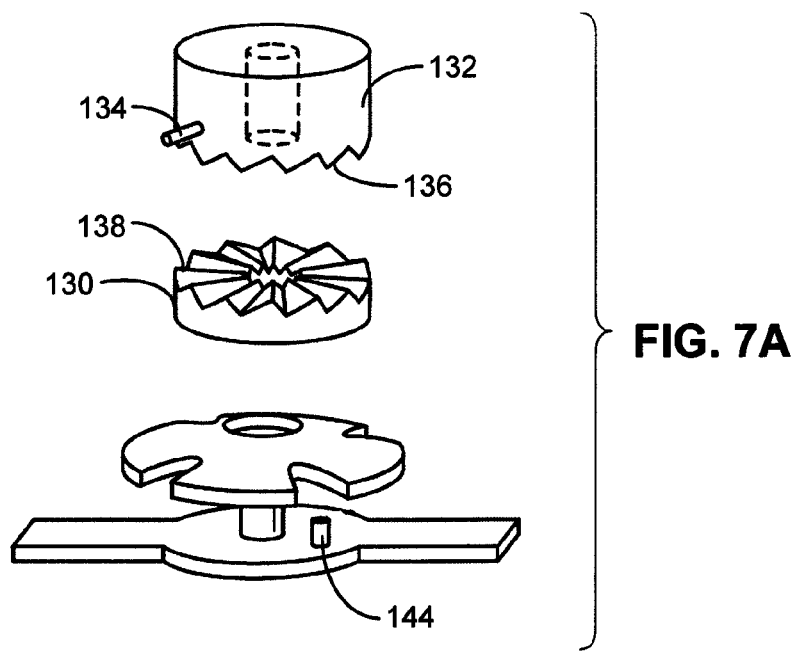
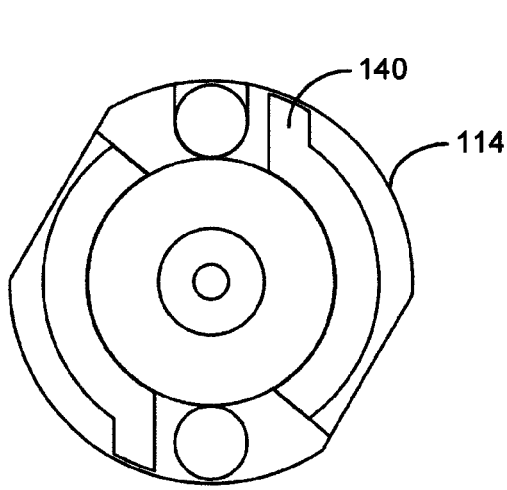
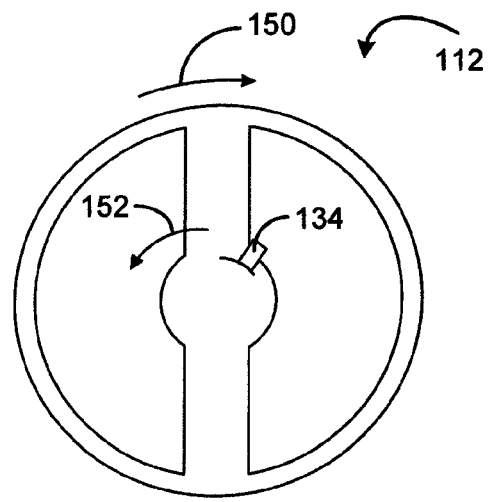
FIG. 7B
FIG. 7C

MEDICAL CUTTING TOOL QUALITY CONTROL SYSTEMS AND METHODS

CROSS REFERENCE TO RELATED APPLICATION

This application claims the benefit of U.S. Provisional Application No. 61/564,263, which was filed on Nov. 28, 2011, and is incorporated herein by reference in its entirety.

FIELD

This disclosure relates to systems and methods for limiting the number of uses of cutting tools and determining the effective functional life of the same.

BACKGROUND

There are many surgical procedures which require the removal and/or cutting of bone in a patient. Such procedures often involve the use of specific cutting tools. For example, in some procedures, specific cutting tools can be provided to ream the internal canal of bones for preparation of implants or to ream the outer surfaces of bones for preparation of implants and drilling holes for bone screw fixation. Conventional cutting tools, however, generally provide no mechanism for identifying the quality or state of the cutting tool. As a result, many cutting tools are disadvantageously used until they no longer function properly.

SUMMARY

Various systems and methods for providing quality control of cutting tools are described herein. In some embodiments, the number of uses of cutting tools can be restricted to ensure the quality of the cutting tool prior to its use for its intended purpose. In other embodiments, the effective functional life of cutting tools can be analyzed and determined to ensure that the number of uses of the tool do not exceed the tool's effective functional life.

In one embodiment, a cutting tool has a cutting surface on a first side of the cutting tool and an attachment member on a second side of the cutting tool. The attachment member is configured to be coupled to a powered driving member. The cutting tool includes a limiting device configured to restrict the use of the cutting tool to a predetermined number of uses. In some embodiments, the limiting device can be configured to restrict the number of uses of the cutting tool by restricting the number of times that the attachment member can be coupled to the powered driving member.

The limiting device can include a counter that is configured to move to a new position each time the attachment member is coupled to the powered driving member. The limiting device can include an activation member having a projection that is configured to engage with a surface of the powered driving member and a surface configured to engage with the counter. The activation member can be configured to move between a first position when the attachment member is not coupled to the powered driving member and a second position when the attachment member is coupled to the powered driving member.

In some embodiments, a spring member can be provided in contact with the activation member to bias the activation member back towards the first position. The attachment member can include a cross bar that extends across the second side of the cutting tool. The cross bar can have an extension member that extends from a surface of the cross bar. The counter can include an opening that extends at least partly through a portion of the counter, with the extension member being positioned to extend through the opening. The counter can be configured to rotate with the extension member extending through the opening until the extension member contacts a side wall that defines a portion of the opening. The opening can be sized to allow a predetermined number of incremental rotations of the counter relative to the cross bar until the extension member contacts the side wall and restricts further movement of the counter relative to the cross bar.

In some embodiments, the first and second sides are on opposite sides of the cutting tool. In some embodiments, the cutting tool can be an acetabular reamer. In some embodiments, the predetermined number of uses can be representative of the effective functional life of the cutting tool. In some embodiments, the counter comprises a longitudinally moveable member.

In another embodiment, a cutting system is provided. The system can include a cutting tool and a drive shaft. The cutting tool can include a cutting surface on a first side of the cutting tool and an attachment member on a second side of the cutting tool. The drive shaft can include a receiving area and a coupling member, with the receiving area being configured to receive the attachment member and the coupling member being configured to secure the cutting tool to the drive shaft. The cutting tool can include an integrated limiting device configured to restrict the number of uses of the cutting tool by restricting the number of times that the attachment member can be coupled to the powered driving member. In some embodiments, the cutting tool can be an acetabular reamer and the drive shaft can be a reamer shaft.

The limiting device can include a counter member that is configured to rotate and/or translate longitudinally one increment to a new position each time the attachment member is coupled to the drive shaft. The limiting device can also include an activation member having a projection that is configured to engage with a surface of the drive shaft to move between a first position when the attachment member is not coupled to the drive shaft and a second position when the attachment member is coupled to the drive shaft. The activation member can be positioned in contact with the counter member so that movement from the first position to the second position causes the counter member to advance the one increment. The attachment member can include a cross bar, wherein the cross bar and the counter member are configured to engage with one another to permit a limited amount of relative movement between the cross bar and the counter member. The limited amount of movement can comprise a predetermined number of increments. The predetermined number of increments can be the number of uses of the cutting tool within its effective functional life.

In other embodiments, a method of restricting the number of uses of a cutting tool is provided. The method can include coupling an attachment member of a cutting tool to a receiving area of a powered driving member, with the coupling of the attachment member to the receiving area comprising rotating the cutting tool relative to the powered driving member. The relative rotation of the cutting tool and powered driving member can cause an activation member on the cutting tool to contact a surface of the powered driving member, with the contact of the activation member with the surface of the powered driving member causing the activation member to move from a first position to a second position. A counter on the cutting tool can be incremented by the movement of the activation member from the first position to the second position. The cutting tool can be removed from the receiving area of the powered driving member. Further coupling of the attachment member to the receiving area of the powered driving member can be restricted once a predetermined number of incrementing steps have occurred.

In some embodiments, the counter on the cutting tool comprises a counter gear that rotates one increment each time the activation member moves from the first position to the second position. The restricting step can include restricting rotation of the counter gear once the predetermined number of incrementing steps have occurred. The restricting of the rotation of the counter gear can be achieved, in some embodiments, by positioning a non-movable engagement member on the cutting tool, with the non-moveable engagement member extending through at least a portion of an opening in the counter gear. The non-moveable engagement member and opening in the counter gear permit relative movement between the counter gear and the non-moveable engagement member when the predetermined number of incrementing steps have not occurred and restrict relative movement between the counter gear and the non-moveable engagement member when the predetermined number of incrementing steps have occurred. A length of the opening in the counter gear can at least partly determine the predetermined number of incrementing steps.

In another embodiment, a method of determining an effective functional life of a medical cutting tool for cutting through bone is provided. The method includes (a) cutting through bone in a bone preparation area using the cutting tool; (b) measuring a temperature of the bone in the bone preparation area; (c) cutting through bone in a different bone preparation area; and (d) measuring a temperature of the bone in the different bone preparation area. Steps (a)-(d) can be repeated until the temperature in a bone preparation area is measured to exceed 50° C. Then, the number of bone preparation areas that can be prepared using the cutting tool until the temperature in a respective bone preparation area exceeds 50° C. can be calculated and the effective functional life of the cutting tool as the number calculated can be identified.

The foregoing and other objects, features, and advantages of the invention will become more apparent from the following detailed description, which proceeds with reference to the accompanying figures.

BRIEF DESCRIPTION OF THE DRAWINGS

FIG. 4B illustrates a cutting tool and a drive shaft to which the cutting tool can be coupled.

FIG. 4C illustrates a cutting tool that can be coupled to a drive shaft.

FIG. 7A illustrates another exploded view of a limited-use cutting tool, shown without the cutting reamer for clarity.

FIG. 7B illustrates a bottom view of the limited-use cutting tool shown in FIG. 7A.

FIG. 7C illustrates a bottom view of the limited-use cutting tool shown in FIG. 7A.

DETAILED DESCRIPTION

Figure 1:
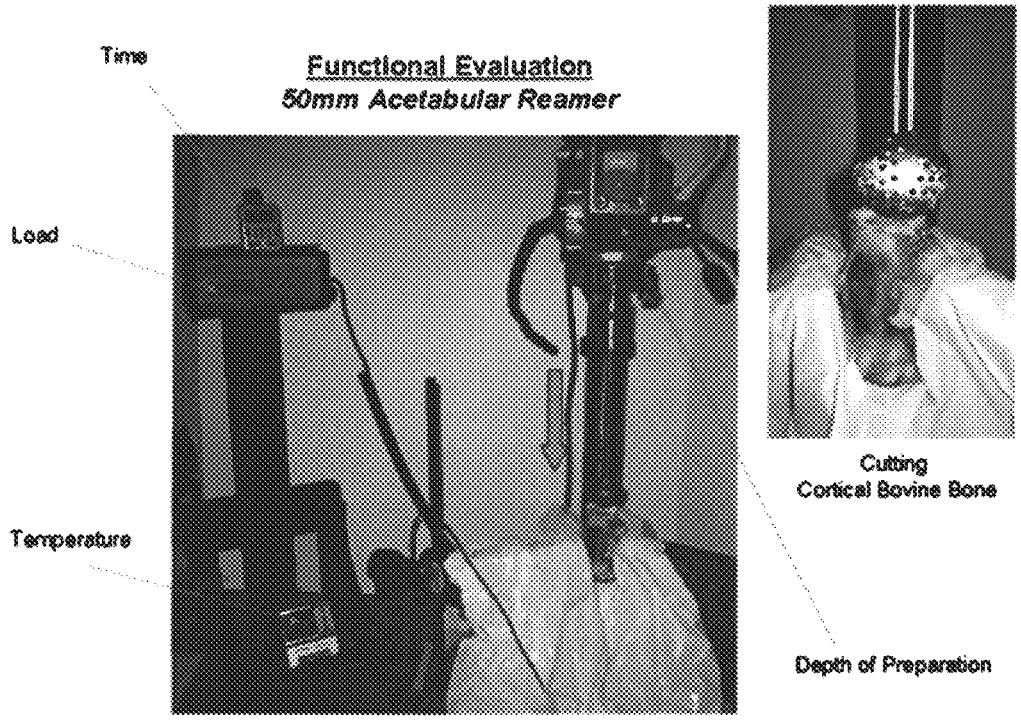
FIG. 1 is illustrates an exemplary test set-up for calculating the number of uses of a cutting tool before it reaches the end of its effective functional life.

Various embodiments of methods and systems for providing improved quality control relating to the use of various instruments and tools are disclosed herein. The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the terms "a," "an," and "the" include both the singular and plural forms of the element(s) they refer to unless the context clearly dictates otherwise. Additionally, the term "includes" means "comprises." As used herein, the term "effective functional life" means the amount of use a tool can experience before it begins to operate suboptimally for its intended purpose. In some embodiments, the effective functional life can be based on a number of uses of the tool and/or an amount of time the tool has been used.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

The technologies described herein can be used with a variety of instruments and tools to ensure that the quality of those instruments and tools are sufficient for the purpose to which they are intended to be used. In some disclosed embodiments, the instruments and tools described include medical cutting tools. As described herein, the adoption of these technologies in connection with medical cutting tools can provide significant improvements over conventional methods and systems for assessing the quality and appropriateness of such instruments and tools for use in surgical procedures.

Conventional use of medical cutting tools generally involves one or more of the following steps. The medical cutting tools are manufactured, purchased, and then delivered to the hospital. Upon receipt by the hospital, the cutting tools undergo specific sterilization processes to sterilize the cutting tools before they are introduced into the operating room environment for use on a patient. After use on a patient, the cutting tools can be processed again through the same or similar procedures for cleaning and sterilization. After sterilization, the cutting tools can be used again on another patient. This process can be repeated many times.

Unfortunately, mere visual inspection of a cutting edge or surface of a tool by the surgeon or other related personnel is not an effective method of assessing the effectiveness of a cutting tool. As a result, cutting tools are generally discarded only when the surgeon uses it in a clinical case and recognizes that the tool is no longer functioning properly. With regard to medical cutting tools, the failure to function properly is generally recognized when the surgeon must apply excessive loads to the tool to advance the cutter through the bone of the patient. Such excessive loads generate additional heat at the cutting tool-bone interface, which can result in undesirable bone necrosis.

Once the surgeon recognizes that the tool is no longer functioning properly, the tool is usually taken out of use. Unfortunately, by the time the tool has been identified as no longer functioning properly, it has already been used past its effective functional life. The recognition of the non-functioning of the tool by the surgeon generally occurs when the cutting tool experiences an extreme failure. At this point, however, not only was the tool used past its effective functional life during the surgery where the surgeon recognized the tool was not functioning properly, the cutting tool likely performed inefficiently or suboptimally for several surgeries prior to this event. As a result, conventional methods of sterilization and reuse of cutting tools expose many patients to negative effects, such as bone heat necrosis, from the use of ineffective cutting tools. The exposure of patients to ineffective cutting tools can negatively affect the success of the surgical procedure, both by affecting the surgical process itself as well as the patient's recovery from the surgery.

Accordingly, conventional approaches to sterilization and reuse do not provide sufficient protection to ensure that suboptimal or otherwise inadequate cutting tools are not reused by surgeons. The methods and systems described herein significantly improve the quality control for determining whether it is desirable to reuse a particular cutting tool after one or more previous uses.

Exemplary Negative Effects of Using Dull Cutting Tools

Dull cutting tools can cause clinical issues for patients on which these dull cutting tools are used. The following embodiments relate to medical cutting tools; however, it should be understood that the systems and methods described herein can be used with other cutting tools in which it would be desirable to limit or otherwise restrict their use when they become ineffective cutting tools.

Medical cutting tools can be used to cut through bone, which can include both cancellous bone (spongy bone) and cortical bone (hard bone). Such cutting tools can include, for example, various reamers configured to cut and/or remove bone from a patient. Efficient cutting tools are desirable to cut through bone, especially cortical bone which is generally denser and stronger than cancellous bone, without creating excessive heat. Excessive heat can cause thermal damage to soft tissue and bone, including bone necrosis, with the amount of thermal damage caused being related to the magnitude of the temperature elevation and the period of time that the tissue is exposed to those temperatures.

Necrosis of bone cells can occur when temperatures generated during cutting actions are at or above 122° F. (50° C.). If the cutting procedure is to be followed by implantation of a prosthetic device into the bone preparation area, the occurrence of bone necrosis can reduce the effectiveness of the device. Such prosthetic devices are desirably supported by strong bone and the occurrence of bone necrosis in the bone preparation area reduces the strength of the bone in that area. This can result in a prosthetic device coming loose from the attachment area when the dead bone is resorbed and replaced by new bone during the healing process.

High temperatures can also negatively affect bone-forming cells (osteoblasts) in the attachment area. The attachment of uncemented orthopaedic devices to bone occurs when new bone grows into or onto the surface of the device. However, bone-forming cells can die when exposed to temperatures over 50° C. Thus, the death of such bone cells at or near the surface of an attachment area can delay and interfere altogether with the attachment process.

Heat generated when cutting bone is primarily due to friction at the cutting edge of the cutter (e.g., teeth) and the movement of bone chips over the surface of the cutter. When a cutting tool is sharp, it can complete the preparation of the bone in fewer revolutions. Since the cutting edges move less distance over the bone, the temperature in the bone preparation area remains lower. In addition, fewer revolutions means that the bone is exposed to the elevated temperatures caused by the cutting action for a shorter period of time. When the cutting edges are dull, however, several issues occur which quickly result in the generation of additional heat from friction. First, the dull condition of cutting edges slows the advancement of the cutting tool and requires greater loads placed on the bone by the cutting tool, both of which contribute to elevating the temperature in the bone preparation area. Second, the cutting tool takes longer to achieve the bone preparation resulting in a greater number of revolutions of the cutting tool at higher applied loads yielding higher temperatures. Because of the greater loads and increased time associated with using dull cutting tools, temperatures associated with their use in cutting bone can exceed the threshold of 122° F.

A cutting tool (e.g., a reamer) that is always sharp is also safer, as less pressure is required when cutting (e.g., reaming). Sharper cutting tools also allow the surgeon to exercise better control and more easily avoid both imprecise and over-cutting (e.g., over-reaming), which can result in improper positioning when the device is implanted, as well as removal of too much bone, compromising the stability of the device and the strength of the remaining bone that supports it.

Effective Functional Life of Instruments

A particular cutting tool can be evaluated to determine the effective functional life of that instrument. After determining the effective functional life of a cutting tool, the systems and methods described herein can restrict the use of that tool outside of the tool's effective functional life. By using the systems and methods described herein, a surgeon (or other operator) can be confident that the cutting tool that is to be used for a cutting process is sufficiently sharp, thereby reducing the occurrence of negative conditions associated with the use of dull instruments, such as bone necrosis when cutting bone.

In some embodiments, the systems and methods disclosed herein provide a limited-use cutting tool to assure quality and function of the tool during a cutting procedure. By using these systems and methods, a simplified quality assurance procedure can be provided which does not require the hospital (or other entity) to implement a more complicated system for tracking and monitoring the condition of a particular cutting tool.

The systems and methods described herein provide various manners of counting the number of uses of a cutting tool and disabling (or otherwise restricting) the use of that tool once the prescribed number of uses has been reached. In some embodiments, the maximum number of uses can be predetermined by, for example, laboratory or field testing. In one embodiment, the simulated clinical conditions can be worsecase scenario conditions. Once the predetermined maximum number of uses has been reached, the cutting tool can be rendered non-functional and can be discarded or otherwise reconditioned.

EXAMPLE

Determination of Effective Functional Life of Cutting Tools

The following example relates to a cutting tool that is an acetabular spherical reamer. The cutting teeth of an acetabular spherical reamer are preferably sharp in order to properly prepare the acetabular bed without generating excessive heat. In many cases, a cutter can work for multiple surgeries; however, the hardness of the bone encountered by the cutter determines how long the cutter will function properly without damaging the patient's bone through heat necrosis. As the cutter encounters hard cortical bone, the cutting edges begin to dull (e.g., teeth cutting edge radii increase) until the cutter will no longer efficiently cut the bone. As the cutting teeth begin to dull, additional force is required to advance the cutter through the bone, thereby generating additional heat which can cause bone necrosis.

FIG. 1 illustrates a laboratory test set-up for determining the effective functional life of a cutting tool. In these tests, acetabular reamers were used to cut bone (i.e., cortical bovine bone) to determine the number of uses the acetabular reamers can experience before the end of their effective functional life. In one example, it was determined that approximately six (6) uses of the reamer produces a complete preparation without generating excessive heat (e.g., temperatures at or above 122° F. (50° C.)).

Figure 2:
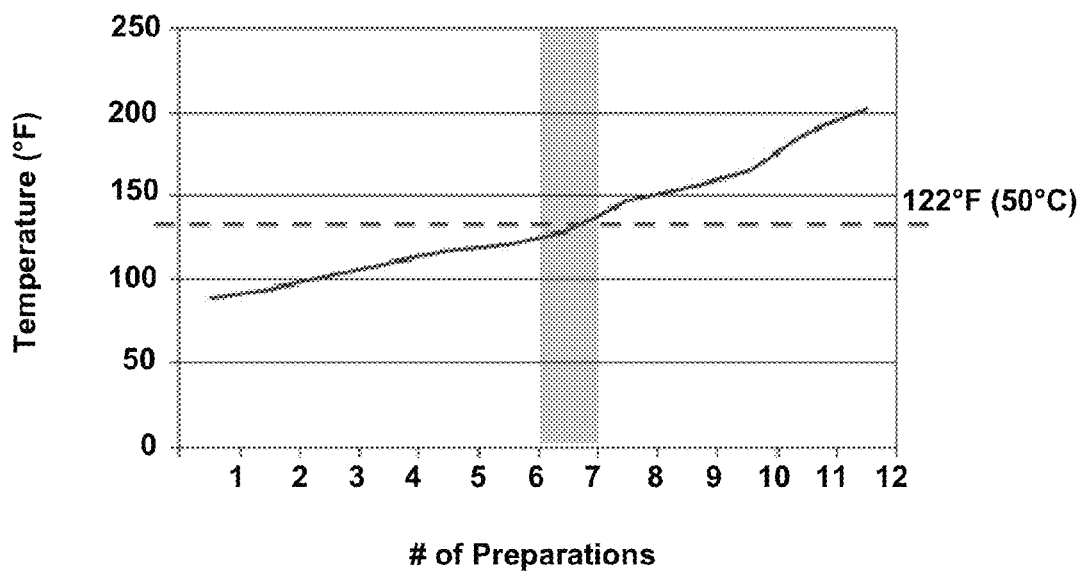
FIG. 2 illustrates a chart of a functional evaluation of a medical cutting tool.
Figure 3:
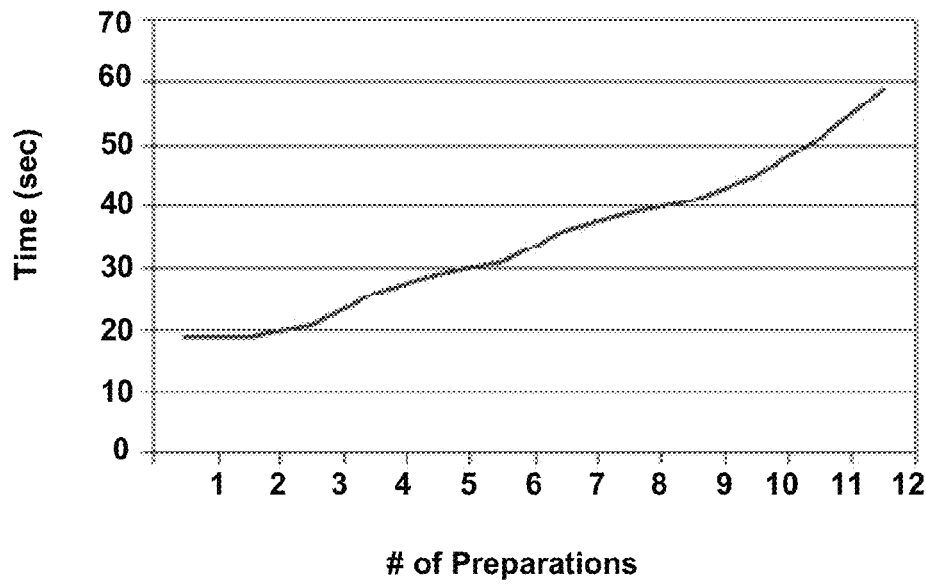
FIG. 3 illustrates another chart of a functional evaluation of a medical cutting tool.
Figure 4A:
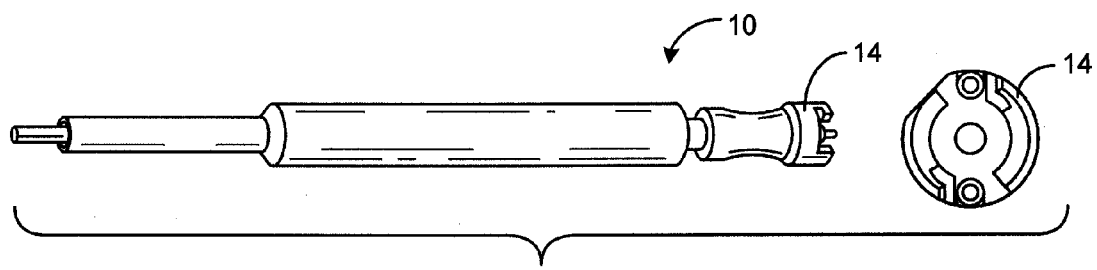
FIG. 4A illustrates a drive shaft to which a cutting tool can be coupled, and an end view of the same.

FIGS. 2 and 3 illustrate the results of an acetabular reamer evaluation in bovine bone. FIG. 2 illustrates a chart showing the functional evaluation of a 50 mm acetabular reamer to cut bovine bone, graphing the number of bone preparations (i.e., uses of the cutting tool) and the temperature in the bone preparation area. FIG. 3 illustrates a chart showing the functional evaluation of a 50 mm acetabular reamer to cut bovine bone, graphing the number of bone preparations (i.e., uses of the cutting tool) and the time required to achieve the bone preparation. As shown in FIGS. 2 and 3, continuing to use the cutter after the sixth use consistently resulted in a longer preparation time and increased heat generation. The sharpness of the teeth cutting edges are directly proportional to the load required to advance the cutter, and therefore the resulting friction/heat generated. As the cutting edge rounds (or dulls), it becomes less effective in penetrating the surface of the bone and requires additional load to attempt to advance it. This cutter wear is generally consistent for all cutting tools.

Exemplary Limited-Use Cutting Tools

In one embodiment, to ensure that an acetabular reamer functions properly during each use (e.g., without causing undue bone necrosis), a limiting device can be provided to limit the number of uses of the reamer. For example, in one embodiment, a limiting device can be provided to limit the number of uses of the reamer to six, which is the number of uses after which it has been determined that this acetabular reamer no longer functions in an optimal manner. The number of uses can vary, however, and can, in some embodiments, be as low as one. The number of uses can be predetermined based on field and/or laboratory testing and can be specific to the cutting device. For example, one acetabular reamer can have an effective functional life that permits six uses of the device to cut bone, while another different acetabular reamer may have an effective life of eight or more.

The limiting device can be incorporated into the acetabular reamer to monitor the number of uses of the instrument by counting the number of times the reamer was assembled to the reamer shaft. Once the prescribed number of uses is reached, the limiting device can prevent the instrument from being assembled to the reamer shaft for further use.

Figure 5A:
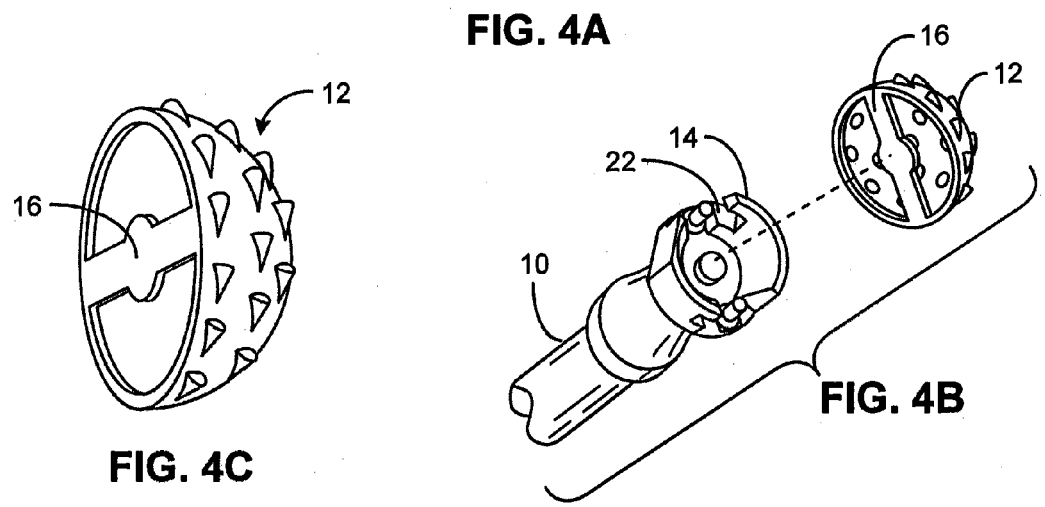
FIGS. 5A-5C illustrate a method of coupling a cutting tool to the drive shaft of FIG. 4A.
Figure 5A:
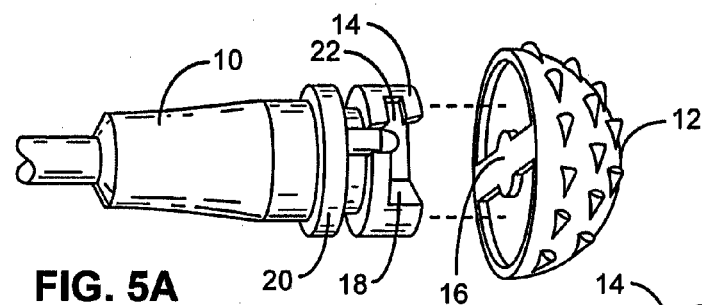
Figure 5B:
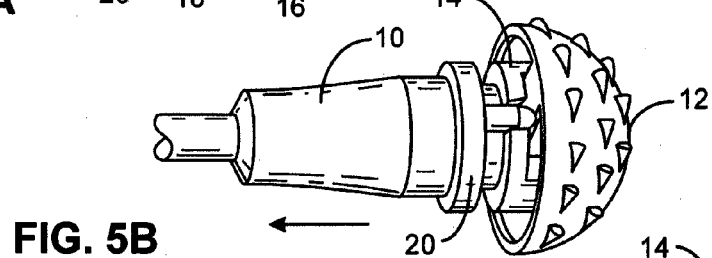
Figure 5C:
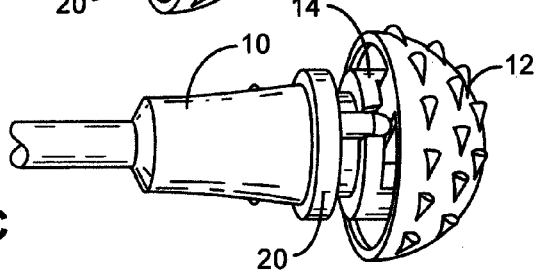

FIGS. 4A-4C and 5A-5B illustrate a reamer shaft 10 and an acetabular reamer 12 that are configured to be coupled together. As shown in FIGS. 4A and 5A-5C, to attach the reamer 12 with the reamer shaft coupling member 14 of the reamer shaft 10, a cross bar 16 of the reamer 12 is aligned with an opening 18 or other mating feature on the reamer shaft coupling member 14. A collar 20 on the reamer shaft 10 can be retracted (FIG. 5A) and the reamer 12 can be inserted into the opening 18 on the reamer shaft 10 (FIG. 5B). To lock the reamer in place, the reamer 12 can be rotated so that the cross bar 16 extends into a slotted portion 22 of the shaft coupling member 14 (e.g., clockwise in FIGS. 5B-5C). Then the retracted collar 20 can be released, moving collar 20 towards the reamer 10 to secure it in place on reamer shaft 12 (FIG. 5C).

Figure 6A:
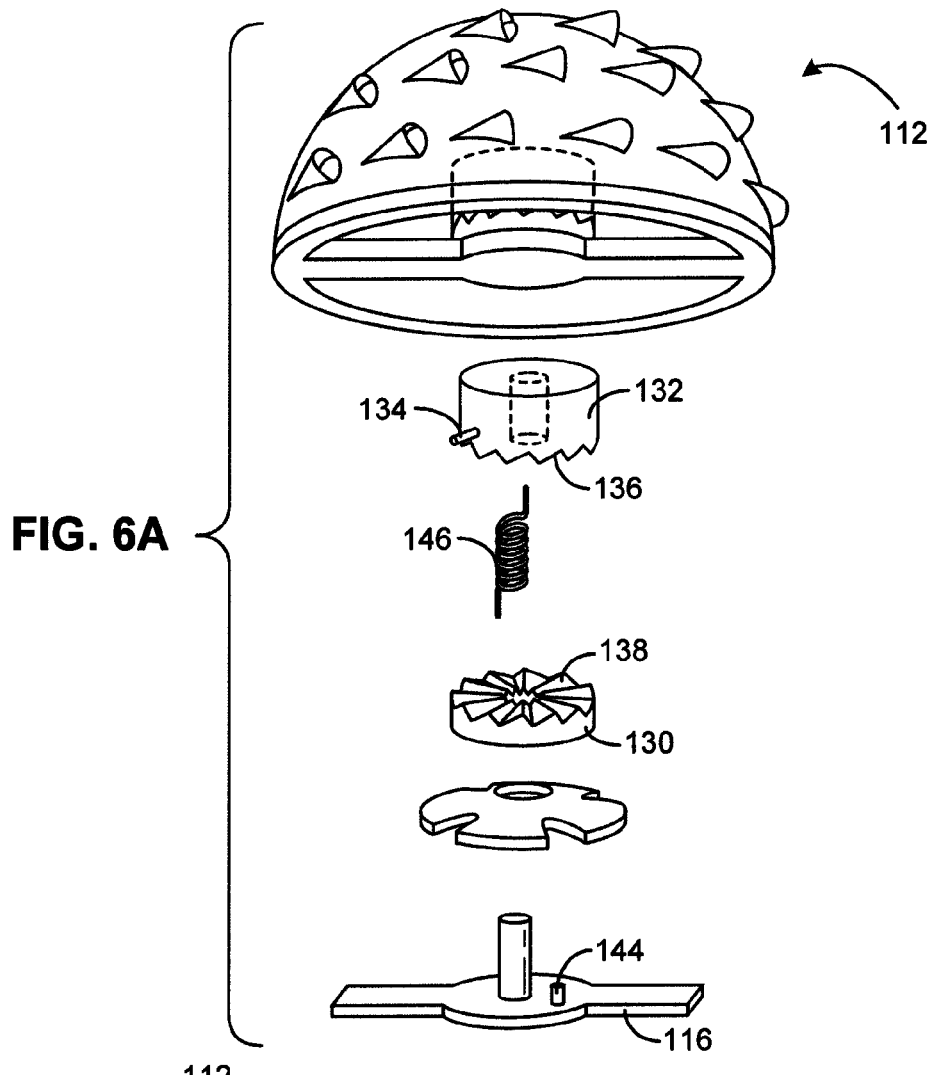
FIG. 6A illustrates an exploded view of a limited-use cutting tool.

FIG. 6A illustrates an embodiment of a limited-use acetabular reamer 112 that can be attached to a reamer shaft, such as that shown in FIGS. 5A-5C. The limited-use reamer 112 comprises a limiting device that restricts the number of uses of the reamer. In one embodiment, the limiting device can function by preventing the attachment of the reamer to a reamer shaft after a certain number of uses.

Figure 6B:
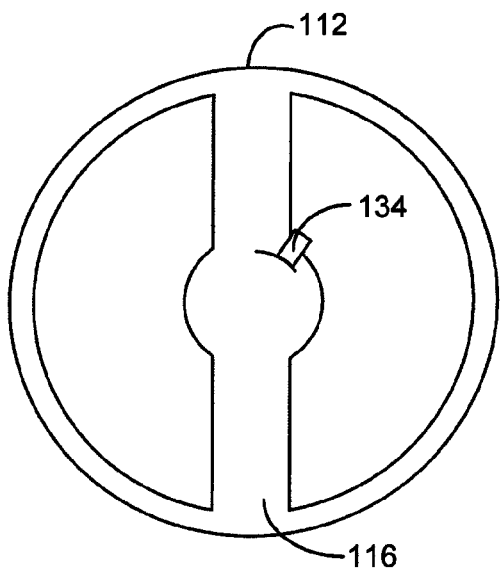
FIG. 6B illustrates a bottom view of the limited-use cutting tool.
Figure 6C:
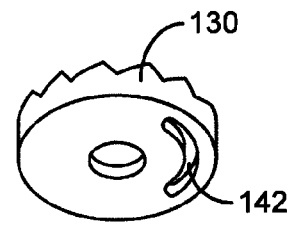
FIG. 6C illustrates a bottom view of a counter gear with a slot formed for receiving a cross bar pin.

The limiting device of the acetabular reamer can comprise a counting mechanism, such as a counter gear 130 shown in FIG. 6A. As shown in FIG. 6, counter gear 130 can be configured to engage with an actuator or activation member 132 that is also coupled to the reamer 112. Actuator 132 can comprise any structure that is configured to engage with the reamer shaft coupling member 114 and cause relative movement in the counter mechanism (e.g., counter gear 130). For example, as shown in FIGS. 6A-6C and 7A-7C, actuator 132 can comprise a pin 134 that extends laterally from a side surface of its main body and a first gear surface 136 configured to mate with a second gear surface 138 of counter gear 132.

When the reamer 112 is coupled to the reamer shaft, the actuator pin 134 is configured to engage with a surface on the reamer shaft (e.g., reamer coupling surface 140). As the reamer 112 is rotated to lock the reamer 132 onto the end of the reamer shaft, contact between the actuator pin 134 and the surface 140 of the reamer shaft causes the actuator pin 134 to rotate, thereby causing the counter gear 130, which is engaged with the actuator 132, to also rotate.

To restrict use of the reamer 112 to a predetermined number of uses, the counter gear 132 is restricted from rotating after that predetermined number of uses has occurred. As shown in FIG. 6C, this can be achieved by providing a slotted portion 142 on a bottom surface of the counter gear 130 that mates with a respective pin member 144 on the surface of the cross bar 116 of the reamer 112. As the counter gear 130 continues to rotate after each use, the pin 144 will move along the slotted portion 142 of the counter gear 130. After a certain number of rotations, however, the counter gear 130 will not be able to rotate any further because the pin 144 will reach the end of the slotted portion 142.

FIG. 7B and FIG. 7C show the interaction of the coupling member 114 with the reamer 112. As shown in FIG. 7C, reamer 112 can be rotated clockwise (in the direction of arrow 150, while actuator pin 134 rests against surface 140 of the coupling member 114. As reamer 112 rotates clockwise, the contact of actuator pin 134 with surface 140 causes actuator 132 to rotate relative to the actuator in the opposite direction (in the relative direction of arrow 152) and engage the counter gear 130. A torsion spring 146 can also be provided to cause the actuator 132 to return to the starting position when the reamer 112 is removed from the reamer shaft. In this manner, when reamer 112 is removed from the shaft, actuator 132 returns to its starting position, but counter gear 130 maintains its position. That is, counter gear 130 moves in only one direction as a result of contact with actuator 132. As counter gear 130 continues to rotate after each use, counter gear 130 will eventually encounter the pin 144 on the cross bar 116. When the pin 144 reaches the end of the slotted portion 142, activator 132 will not be able to rotate any further and reamer 112 will no longer be capable of being assembled on shaft coupling member 114.

The number of times of use can be adjusted by changing the length of travel for each use and/or changing the length of permissible travel of the pin within the slotted portion (e.g., by lengthening or shortening the slotted portion). In addition, the engaging surfaces of the counter gear and cross bar can be roughened to increase the friction between those two surfaces to achieve more effective contact between those two surfaces. In the embodiment shown in FIGS. 6A-6C, the actuator is configured to rotate the counter gear about 36 degrees for each use; however, other amounts of travel per use can be achieved using actuator and counter gears as described herein.

Although this embodiment provides a non-movable member on the cross bar and a slotted member on the counter gear, it should be understood that different configurations are possible, including, for example, providing a rigid member on the counter gear that engages with a non-movable slotted section or the like otherwise positioned on the cutting tool and/or reamer shaft.

In some embodiments, the number of uses can be varied based on the size of the gearing and/or the length of the slotted portion. For example, a longer slotted portion permits a greater number of uses, while a shorter slotted portion allows fewer uses.

When the reamer is removed from the reamer shaft, the actuator can be configured to return to its original starting position. To facilitate this movement of the actuator, a spring, such as a torsion spring, can be positioned in contact with the actuator.

Preferably, the limiting device is built-in to the cutting tool so that the counting measures of the device cannot be easily circumvented. For example, in the embodiment described in FIGS. 5 and 6, the limiting device is coupled to the reamer itself so that the limiting device is a part of the structure of the reamer.

It should be understood that alternative limiting devices and systems can be used to restrict the number of times that an instrument can be attached to another tool. For example, FIGS. 8-11 illustrate two other embodiments of instruments that comprise limiting devices that are configured to prevent coupling of an instrument after a predetermined number of uses.

Figure 8A:
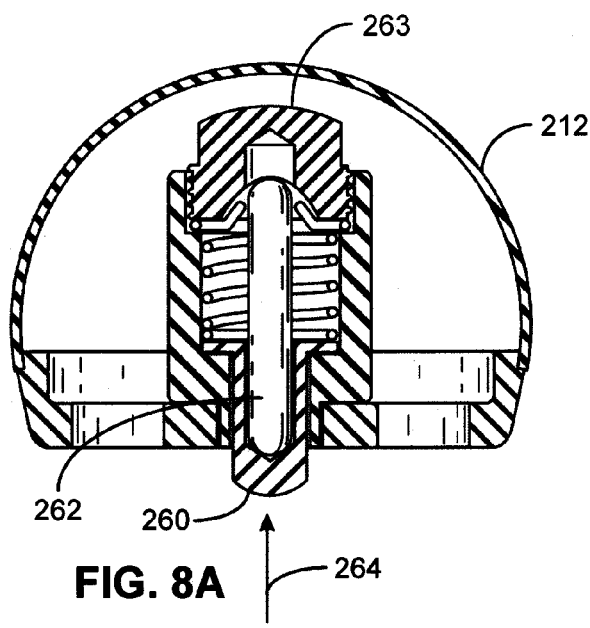
FIGS. 8A-8C illustrate a method of using a limited-use cutting tool.
Figure 8B:
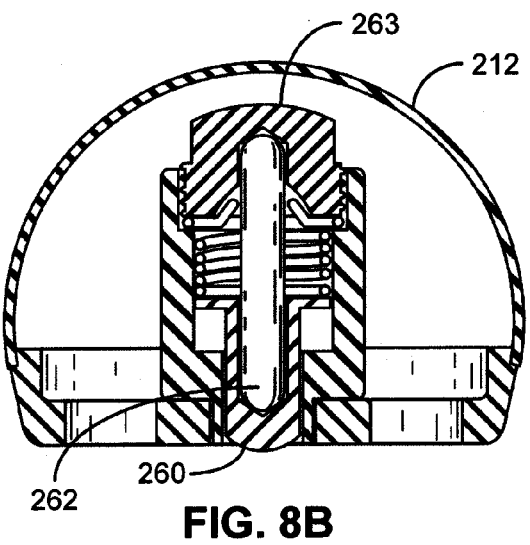
Figure 8C:
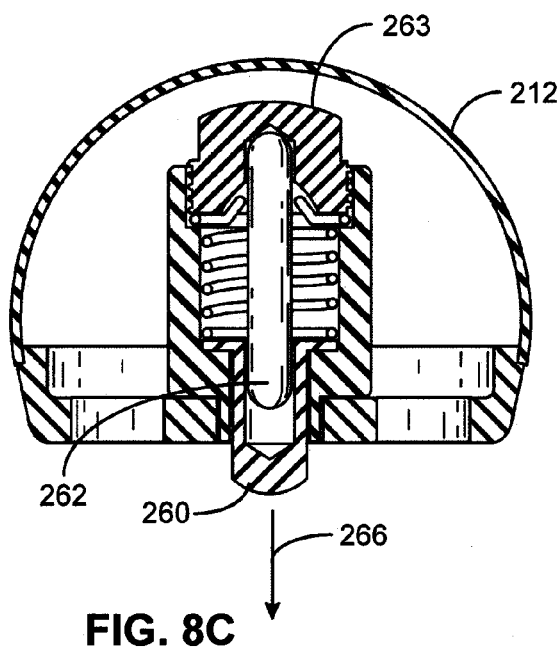

FIGS. 8A-8C illustrate an embodiment of an instrument that includes a limiting device that has longitudinal counting mechanism, rather than a rotational counting mechanism, that is configured to restrict the number of times the instrument can be coupled to a tool. In the example shown in FIGS. 8A-8C, the instrument can be a reamer shaft and an acetabular reamer 212 similar to those shown in other embodiments.

As shown in FIG. 8A, the limiting device can include a longitudinally moveable element 260 (e.g., a plunger) that is configured to engage with a surface of the tool to which the instrument is to be attached (e.g., reamer shaft). Upon contact with the surface of the tool, the longitudinally moveable element 260 can contact and move a longitudinal counter that is moveable through a limited distance to restrict the number of times the instrument has been attached to the tool.

As shown in FIGS. 8A-8C, the longitudinal counter can be a longitudinally moveable counting rod 262 that can move a predetermined distance within the instrument. Each time the longitudinally moveable element 260 contacts the counting rod 262, the counting rod 262 moves a predetermined distance until it reaches the end of the amount of travel that is permitted by the instrument. For example, counting rod can be configured so that it can move a predetermined distance within an opening in an end cap 263. Once the counting rod has traveled the predetermined distance, an end of the counting rod engages with the end cap. As a result of the engagement of the counting rod with the end cap, when the longitudinally moveable element 260 engages with a surface on the tool, the counting rod cannot move any further within the opening in the end cap and further assembly of the instrument to the tool is prevented.

FIG. 8A illustrates movement of longitudinally moveable element 260 in the direction of arrow 264 upon engagement of the longitudinally moveable element 260 with a reamer shaft. As shown in FIG. 8B, the reamer is then rotated to lock it in place (as described in other embodiments) and longitudinal counter 262 advances a prescribed distance. As shown in FIG. 8C, upon removal of the reamer from the shaft, the longitudinally moveable element 260 returns to the start position (moving in the direction of arrow 266) so that the cycle can repeat. Once the longitudinally moveable element 260 reaches the end of the cap (or some other limiting structure), further assembly of the reamer to the shaft is no longer possible.

The number of uses of the instrument can be set by determining the distance that the counting rod will travel during each engagement of the longitudinally moveable element with the surface of the tool, and setting the total distance that the counting rod can travel within the instrument to be that distance times the number of uses of the instrument that are permissible before the instrument exceeds its effective functional life.

Figure 9:
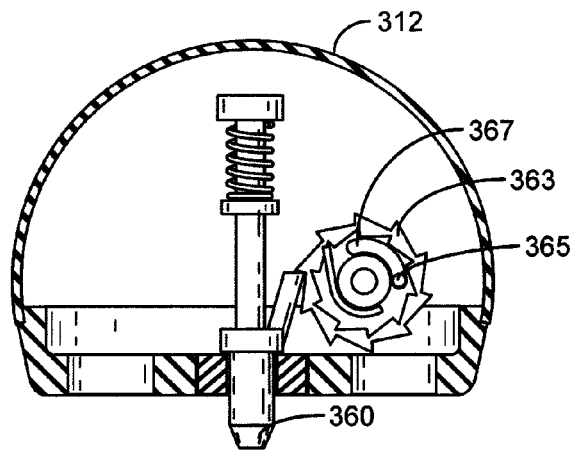
FIG. 9 illustrates a system with an indexing wheel for limiting the number of uses of a cutting device.

Another alternative embodiment of an instrument with a limiting device is shown in FIG. 9. In this embodiment, a combination of longitudinal movement and rotation movement can be used to count and restrict the number of uses of the instrument. As shown in FIG. 9, a longitudinally moveable member 360 (e.g., a plunger) is configured to engage with a circular counter. The circular counter can comprise, for example, an indexing wheel 363 that is rotatably attached to the instrument. For each engagement of the instrument (e.g., an acetabular reamer) with a tool (e.g., a reamer shaft), the indexing wheel 363 can rotate by a predetermined amount. In some embodiments, the predetermined amount of rotation for each use of the instrument (i.e., for each engagement of the instrument to a tool) can be a single tooth of the indexing wheel. In other embodiments, the predetermined amount of rotation for each use of the instrument can be a rotation through a plurality of teeth on the indexing wheel.

After a predetermined number of uses have been achieved (e.g., the number of uses that have been determined to be possible before exceeding the effective functional life of the instrument), a pin or other restricting member located on the instrument can be configured to contact another structure to restrict further movement of the indexing wheel. When the indexing wheel can no longer rotate, the instrument can no longer be coupled with the tool because the plunger cannot be depressed.

Thus, relative movement of the indexing wheel and plunger can be restricted to prevent attachment of the instrument to a tool for further use of the instrument. In the embodiment shown in FIG. 9, a pin 365 is fixed to the instrument (e.g., reamer body) and a groove 367 in the indexing wheel permits a predetermined amount of rotational movement of the indexing wheel 363 relative to the pin 365. However, it should be understood that the relative movement between the indexing wheel and the instrument can be restricted in a variety of other ways.

Figure 10A:
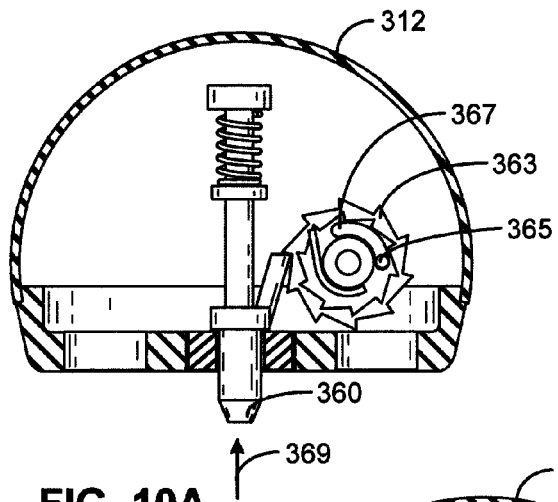
FIGS. 10A-10C illustrate a method of using a limited-use cutting tool.
Figure 10B:
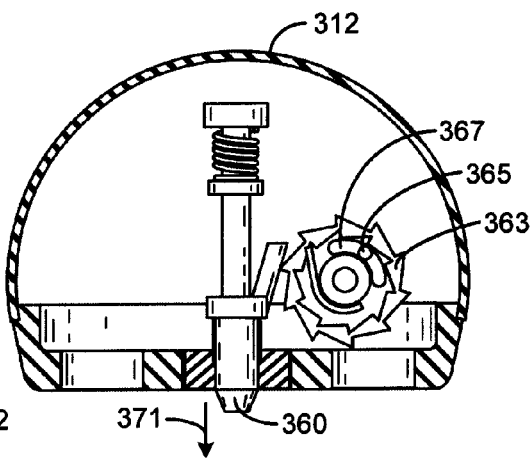
Figure 10C:
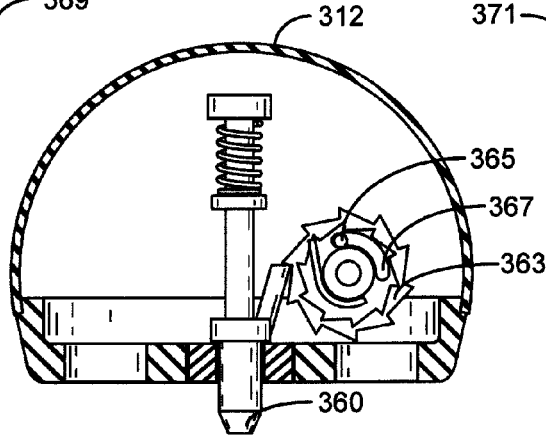

FIGS. 10A-10C illustrate the operation of the limiting use member of this embodiment. FIG. 10A illustrates a force being applied by a shaft in contact with the reamer 312 in the direction of arrow 369. As the longitudinally moveable element 360 moves upward in response to the force, it engages with and causes indexing wheel 363 to rotate a predetermined amount. As shown in FIG. 10B, when reamer 312 is removed from the shaft, longitudinally moveable element 360 moves downwards (in the direction of arrow 371). As the longitudinally moveable element 360 moves downward it does not engage with indexing wheel 363. Then, FIG. 10C illustrates the indexing wheel 363 in a position where the reamer 312 can no longer be received on a shaft because pin 365 has reached the end of its travel along groove 367.

In some embodiments, an indicator can be provided to reflect the number of remaining uses and/or to visually provide a user with an indication that the current use of the reamer is its last use within its effective functional life.

Figure 11A:
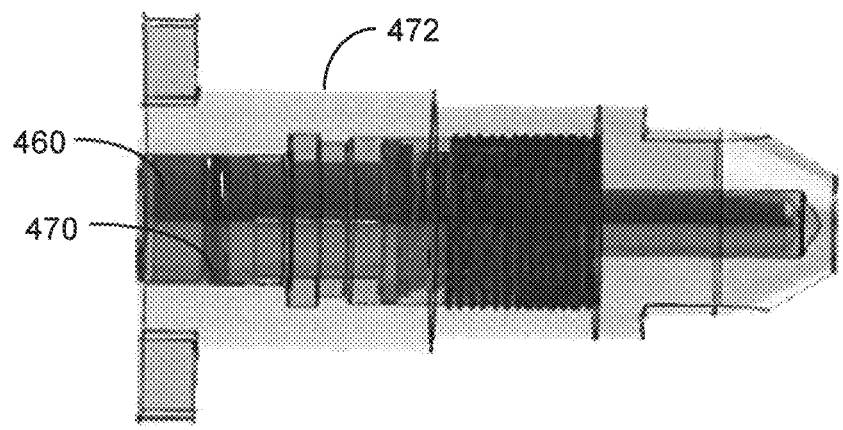
FIGS. 11A-11B illustrate a method of using a limited-use cutting tool.
Figure 11B:
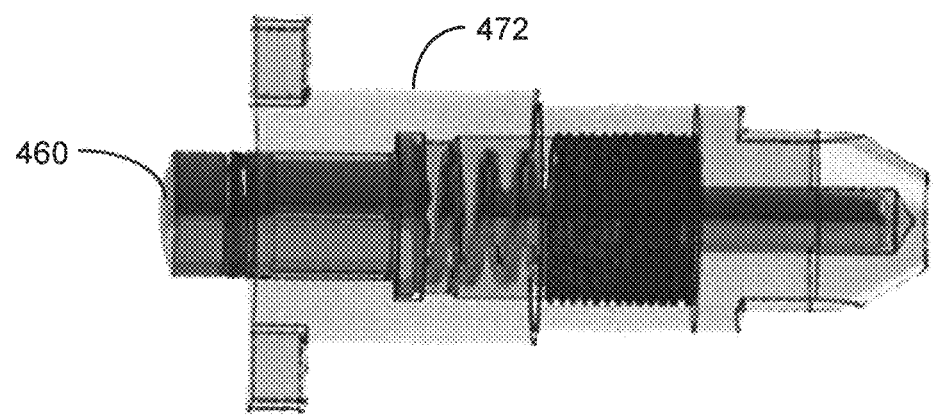

FIGS. 11A and 11B illustrate an embodiment that provides a visual indication that the reamer has reached a predetermined number of uses that indicate it is at the end of its effective functional life. FIGS. 11A and 11B show an embodiment where the visual indicator (e.g., a red O-ring) moves from a position inside the device to a position outside the device where it is visible. In this embodiment, an O-ring 470 can be provided inside the drive shaft 472 of a reamer. Once the device reaches its last use and is removed from the reamer shaft, an inner spring 474 pushes the longitudinally moveable element 460 and the O-ring 470 out of the end of the device providing a visual indication that the reamer cannot be used again.

It should be understood that the systems and methods described herein can be applied to a variety of cutting tools with different couplings. Thus, as discussed herein, different cutting tools can be provided with limiting devices that can limit the use of the cutting tool to a predetermined number of uses, based on a determined effective functional life of that device for its intended function. By using the systems and methods described herein, various cutting tools can be provided with built-in limiting devices to provide quality control procedures that are tied to the number of uses of the tools and not on visual inspection or other efforts by surgeons or other related personnel.

Thus, the embodiments described herein advantageously register (by counters or other similar mechanisms) the number of uses of an instrument such as a cutting tool by tracking or monitoring the number of times the instrument has been coupled to another member (e.g., a drive shaft). Because an instrument may be sterilized many times before use, the registering of "uses" instead of "sterilizations" can be advantageous. For example, for any surgical procedure numerous sterilized instruments may be packaged together for the surgeon, such as various size reamers in a single sterilized tray. However, generally not all of these sterilized instruments are assembled with a tool (e.g., a drive shaft) and used by the surgeon. Thus, by registering the number of times of assembly, the effective functional life of the instrument can be accurately tracked.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A cutting tool comprising:
a cutting surface on a first side of the cutting tool;
an attachment member on a second side of the cutting tool, the attachment member being configured to be coupled to a powered driving member; and
a limiting device configured to restrict the use of the cutting tool to a predetermined number of uses.

2. The cutting tool of claim 1, wherein the limiting device is configured to restrict the number of uses of the cutting tool by restricting the number of times that the attachment member can be coupled to the powered driving member.

3. The cutting tool of claim 2, wherein the limiting device comprises a counter that is configured to move to a new position each time the attachment member is coupled to the powered driving member.

4. The cutting tool of claim 3, wherein the limiting device further comprises an activation member having a projection that is configured to engage with a surface of the powered driving member and a surface configured to engage with the counter, the activation member being configured to move between a first position when the attachment member is not coupled to the powered driving member and a second position when the attachment member is coupled to the powered driving member.

5. The cutting tool of claim 4, further comprising a spring member, the spring member being in contact with the activation member to bias the activation member back towards the first position.

6. The cutting tool of claim 1, wherein the cutting tool comprises an extension member that extends from a surface of the cutting tool and the counter comprises an opening that extends at least partly through a portion of the counter, the extension member being positioned to extend through the opening, and
wherein the counter is configured to rotate with the extension member extending through the opening until the extension member contacts a side wall that defines a portion of the opening.

7. The cutting tool of claim 6, wherein the extension member extends from a cross bar that extends across the second side of the cutting tool.

8. The cutting tool of claim 6, wherein the opening is sized to allow a predetermined number of incremental rotations of the counter relative to the extension member until the extension member contacts the side wall and restricts further movement of the counter relative to the extension member.

9. The cutting tool of claim 1, wherein the first and second sides are on opposite sides of the cutting tool.

10. The cutting tool of claim 1, wherein the cutting tool comprises an acetabular reamer.

11. The cutting tool of claim 1, wherein the predetermined number of uses comprises an effective functional life of the cutting tool.

12. The cutting tool of claim 3, wherein the counter comprises a longitudinally moveable member.

13. The cutting tool of claim 3, wherein the counter comprises a visual indicator that the predetermined number of uses has been reached.

14. A cutting system comprising:
a cutting tool comprising a cutting surface on a first side of the cutting tool and an attachment member on a second side of the cutting tool; and
a drive shaft having a receiving area and a coupling member, the receiving area being configured to receive the attachment member and the coupling member being configured to secure the cutting tool to the drive shaft,
wherein the cutting tool comprises an integrated limiting device configured to restrict the number of uses of the cutting tool by restricting the number of times that the attachment member can be coupled to the powered driving member.

15. The cutting system of claim 13, wherein the cutting tool comprises an acetabular reamer and the drive shaft comprise a reamer shaft.

16. The cutting system of claim 13, wherein the limiting device comprises a counter member that is configured to move one increment to a new position each time the attachment member is coupled to the drive shaft.

17. The cutting system of claim 16, wherein the limiting device further comprises an activation member having a projection that is configured to engage with a surface of the drive shaft to move between a first position when the attachment member is not coupled to the drive shaft and a second position when the attachment member is coupled to the drive shaft, the activation member being positioned in contact with the counter member so that movement from the first position to the second position causes the counter member to advance the one increment.

18. The cutting system of claim 17, wherein the counter member rotates to move one increment to a new position.

19. The cutting system of claim 17, wherein the counter member translates longitudinally to move one increment to a new position.

20. The cutting system of claim 17, wherein the attachment member comprises a cross bar, the cross bar and the counter gear being configured to engage with one another to permit a limited amount of relative movement between the cross bar and the counter member, the limited amount of movement comprising a predetermined number of increments.

21. The cutting system of claim 20, wherein the predetermined number of increments comprises the number of uses of the cutting tool within its effective functional life.

22. A method of restricting the number of uses of a cutting tool, the method comprising:
coupling an attachment member of a cutting tool to a receiving area of a powered driving member, the coupling of the attachment member to the receiving area comprising rotating the cutting tool relative to the powered driving member;
causing, by the relative rotation of the cutting tool and powered driving member, an activation member on the cutting tool to contact a surface of the powered driving member, the contact of the activation member with the surface of the powered driving member causing the activation member to move from a first position to a second position;
incrementing a counter on the cutting tool by the movement of the activation member from the first position to the second position;
removing the cutting tool from the receiving area of the powered driving member; and
restricting further coupling of the attachment member to the receiving area of the powered driving member once a predetermined number of incrementing steps have occurred.

23. The method of claim 22, wherein the counter on the cutting tool comprises a counter gear that rotates one increment each time the activation member moves from the first position to the second position, the restricting step comprising:
restricting rotation of the counter gear once the predetermined number of incrementing steps have occurred.

24. The method of claim 22, wherein the counter on the cutting tool comprises a counter rod that translates longitudinally one increment each time the activation member moves from the first position to the second position, the restricting step comprising:
restricting longitudinal translation of the counter rod once the predetermined number of incrementing steps have occurred.

25. The method of claim 23, wherein the restricting of the rotation of the counter gear is achieved by positioning a non-movable engagement member on the cutting tool, the non-moveable engagement member extending through at least a portion of an opening in the counter gear, and wherein the non-moveable engagement member and opening in the counter gear permit relative movement between the counter gear and the non-moveable engagement member when the predetermined number of incrementing steps have not occurred and restrict relative movement between the counter gear and the non-moveable engagement member when the predetermined number of incrementing steps have occurred.

26. The method of claim 25, wherein a length of the opening at least partly determines the predetermined number of incrementing steps.

27. The method of claim 22, further comprising providing a visual indication that the predetermined number of incrementing steps have occurred.

28. The method of claim 27, wherein the providing of the visual indication comprises moving an indicator from inside of the cutting tool to outside of the cutting tool where it is visible to a user.

29. A method of determining an effective functional life of a medical cutting tool for cutting through bone, the method comprising:
(a) cutting through bone in a bone preparation area using the cutting tool;
(b) measuring a temperature of the bone in the bone preparation area;
(c) cutting through bone in a different bone preparation area;
(d) measuring a temperature of the bone in the different bone preparation area;
(e) repeating steps (a)-(d) until the temperature measured exceeds 50° C.;
(f) calculating the number of bone preparation areas that can be prepared using the cutting tool until the temperature in a respective bone preparation area exceeds 50° C.; and
(g) identifying the effective functional life of the cutting tool as the number calculated in step (f).

* * * * *